United States Patent
Olsen

[11] Patent Number: 5,951,532
[45] Date of Patent: Sep. 14, 1999

[54] COLLECTING BAG SYSTEM COMPRISING SUCH A BAG AND AN BAG EXTENSION FOR SUCH A SYSTEM

[75] Inventor: Hans Olsen, Hørsholm, Denmark

[73] Assignee: Coloplast A/S, Denmark

[21] Appl. No.: 08/860,416

[22] PCT Filed: Dec. 21, 1995

[86] PCT No.: PCT/DK95/00513

§ 371 Date: Jun. 23, 1997

§ 102(e) Date: Jun. 23, 1997

[87] PCT Pub. No.: WO96/19954

PCT Pub. Date: Jul. 4, 1996

[30] Foreign Application Priority Data

Dec. 23, 1994 [DK] Denmark ................................. 1480/94

[51] Int. Cl.$^6$ ........................................................ A61F 5/44
[52] U.S. Cl. ........................... 604/332; 604/334; 604/338; 604/339
[58] Field of Search ..................... 604/332, 334, 604/335, 337, 339, 341, 342

[56] References Cited

U.S. PATENT DOCUMENTS

| | | | |
|---|---|---|---|
| 2,669,235 | 2/1954 | Burton | 604/334 |
| 3,825,005 | 7/1974 | Fenton | 128/283 |
| 4,280,498 | 7/1981 | Jensen | 128/283 |
| 4,319,571 | 3/1982 | Winchell | 128/283 |
| 4,553,967 | 11/1985 | Ferguson et al. | 604/334 |
| 4,784,656 | 11/1988 | Christiean | 604/334 |
| 4,834,732 | 5/1989 | Steer et al. | 604/342 |
| 5,593,397 | 1/1997 | La Gro | 604/355 |

FOREIGN PATENT DOCUMENTS

| | | |
|---|---|---|
| 114425 | 6/1969 | Denmark . |
| 1449518 | 7/1966 | France . |
| 1447314 | 8/1976 | United Kingdom . |
| 1474435 | 5/1977 | United Kingdom . |
| 93/17642 | 9/1993 | WIPO . |

Primary Examiner—Ronald Stright
Assistant Examiner—David J. Cho
Attorney, Agent, or Firm—Ostrolenk, Faber, Gerb & Soffen, LLP

[57] ABSTRACT

A collecting bag system for human body wastes comprises a collecting bag with a bag element formed by two predominantly oblong plastic film blanks with joined edges and with an inlet opening surrounded by connecting elements for connection to a body orifice, particularly a stoma, and a closeable outlet opening in an end section of one plastic film blank. The outlet opening is surrounded by a coupling ring with an outwardly facing engagement flange, and the system further comprises a bag extension with a coupling ring with a corresponding inward-facing engagement element for dismountable, sealing coupling to the coupling ring of the outlet opening. On the inside of the coupling ring of the outlet opening a closing membrane is placed with an annular coupling element for a sealing, but releasable coupling with an inward-facing engagement element on the coupling ring of the outlet coupling.

15 Claims, 3 Drawing Sheets

COLLECTING BAG SYSTEM COMPRISING SUCH A BAG AND AN BAG EXTENSION FOR SUCH A SYSTEM

BACKGROUND OF THE INVENTION

The present invention relates to a collecting bag for human body wastes comprising a collecting bag in the shape of a bag member formed by two largely oblong plastic film blanks with joined edges and with an inlet opening surrounded by connecting elements for connection to a body orifice, particularly a stoma, and a closeable outlet opening placed at a distance from the inlet opening.

From GB patent publication No. 1447314 a stoma bag is known, which is intended especially for newly operated patients confined to bed, and which is designed with an outlet opening which through a connecting tube, can be connected to a collecting tank. The coupling between the bag outlet opening and the tube end connected to this opening is for this purpose designed as a rather simple rib or snap fastening interlock, with neither adequate protection against contamination nor satisfactory sealing against the emission of odour.

SUMMARY OF THE INVENTION

The object of the present invention is to provide both a new outlet coupling design and an entirely new concept for coupling with a collecting bag of said type with a bag extension, which can be designed as a coupling tube, but which can also have other designs, and where the collecting bag can also be used on its own without coupling with the bag extension and with a fully adequate sealing against contamination and emission of odour.

For achieving this according to a first aspect of the convention, a collecting bag of said type is characterized in that the outlet opening is made in an end section of one plastic film blank and surrounded by a first coupling ring with an outward-facing engagement flange providing a removable sealing coupling with a second coupling ring with a corresponding inward-facing engagement part, and that on the inside of the first coupling ring a closing membrane is placed with an annular coupling element for a sealing, but releasable coupling with an inward-facing engagement element on the first coupling ring, which closing membrane with coupling element is firmly connected to the other plastic film blank, on the outside of which plastic film blank opposite the coupling element a catcher flap is mounted for release of the coupling between the coupling specimen of the closing membrane and the first coupling ring.

The placing of the outlet opening in the bag and the design of the surrounding first coupling ring provide a safe operation in connection with emptying the bag through the outlet opening, as the passage through the outlet opening for the bag contents is opened entirely by release of the closing membrane. As the second coupling ring can be mounted on the outside of the same plastic film blank of the bag as the first coupling ring, the bag end section can be folded up during use and secured by coupling the first and second sealing rings.

According to another aspect of the invention, a collecting bag system comprising a collecting bag of said type can also include a bag extension, in which the second coupling ring is mounted. After the decoupling of such bag extension, the coupling of the closing membrane with the coupling ring is relatively easy to reestablish after the contents, eg, faeces and air, of the end section of the collecting bag have been pressed into the extension. Coupling and change of a bag extension can thus in all essentials take place without contamination and odour nuisances.

The collecting bag system according to the invention is particularly well suited for newly operated patients confined to bed, for use in nursing homes and for ileostomy patients with uncontrolled release of faeces of a relatively fluid consistency.

To facilitate the use of the collecting bag without the bag extension, it is possible when using the collecting bag in such a system, according to a suitable embodiment of the invention, to attach an exterior coupling ring to said first plastic film blank above said end section for securing the first coupling ring with the end section folded up.

The collecting bag system according to the invention may comprise different forms of bag extensions.

In the same way as for the stoma bag according to the above GB patent publication, a bag extension can thus be designed as a tube of plastic film with said coupling ring mounted in one end. The other tube end can in a suitable way, and preferably by means of coupled coupling rings, be connected to an inlet opening of a collecting bag or tank with larger capacity.

The bag extension itself can also be designed as a collecting bag with larger capacity, a so-called bedside bag, with said coupling ring directly connectable to the coupling ring around the outlet opening of the collecting bag carried by the patient.

As alternative possibilities, the bag extension can be designed as a collecting bag for attachment to the patient's leg or like a disposable discharge bag of a water-soluble film material which can be flushed down the toilet and which is provided with a coupling ring of a biodegradable material.

The collecting bag and bag system according to the invention in its entirety entails a considerable relief of the nursing work in hospitals and nursing homes as well as during home care, since the work involved in changing and possibly emptying conventional stoma bags is reduced considerably whereas the level of hygiene is improved through a reduction of the incidence of contamination requiring a change of bed linen.

In relation to the coupling principle used in the above-mentioned GB patent publication, the invention moreover entails the advantage that, for the coupling, coupling rings are used of a design corresponding to the one known already in connection with stoma bag coupling to the patient's stoma orifice by means of conventional coupling plates. Thus, the use of the collecting bag and bag system according to the invention does not require special and thorough instruction of patients or nursing staff.

BRIEF DESCRIPTION OF THE DRAWINGS

In the following the invention will be explained in further detail with reference to the schematic drawing, in which.

DESCRIPTION OF THE INVENTION

Figure 1:
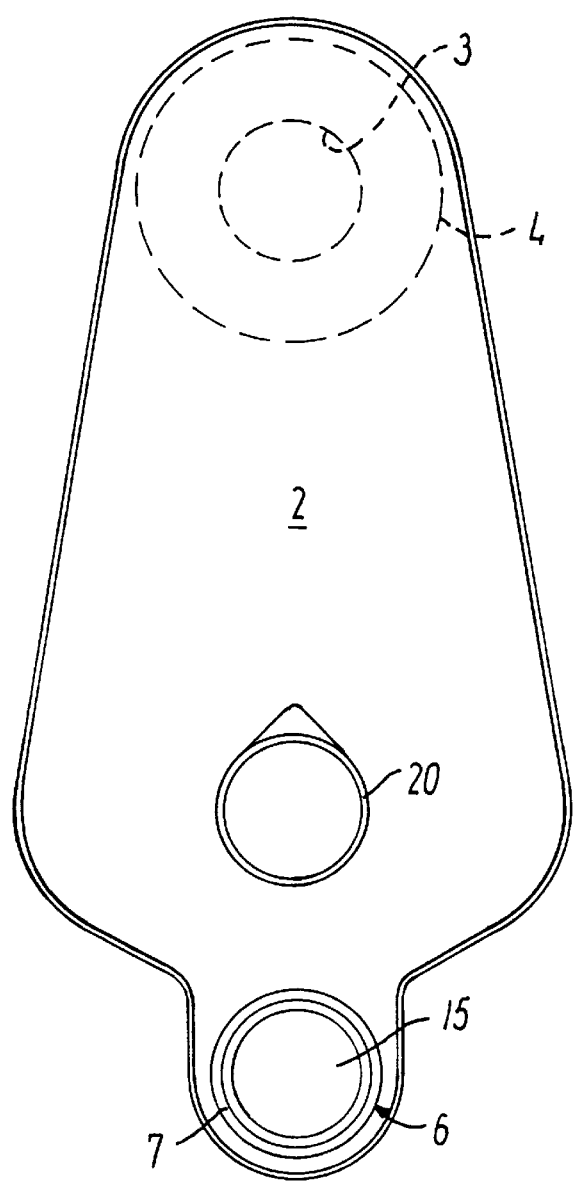
FIGS. 1 and 2 show a plane view and a sectional view of a stoma bag as an embodiment of a collecting bag according to the invention.
Figure 2:
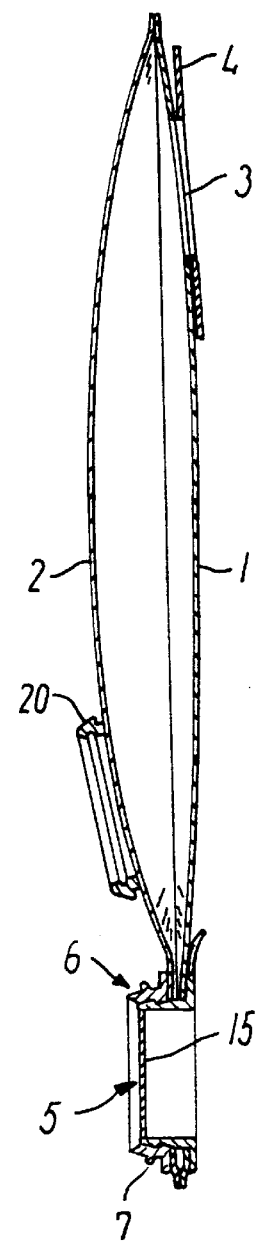

As one example of an embodiment of a collecting bag according to the system of the invention, FIGS. 1 and 2 show a stoma bag of a design, conventional per se, with a bag member formed by two largely oblong plastic film blanks 1 and 2 with joined edges, of which one plastic film blank 1, constituting the back wall of the bag facing the user is designed with an inlet opening 3 surrounded by an adhesive plate 4 known per se for fastening the bag to the skin round a patient's stoma.

Figure 3:
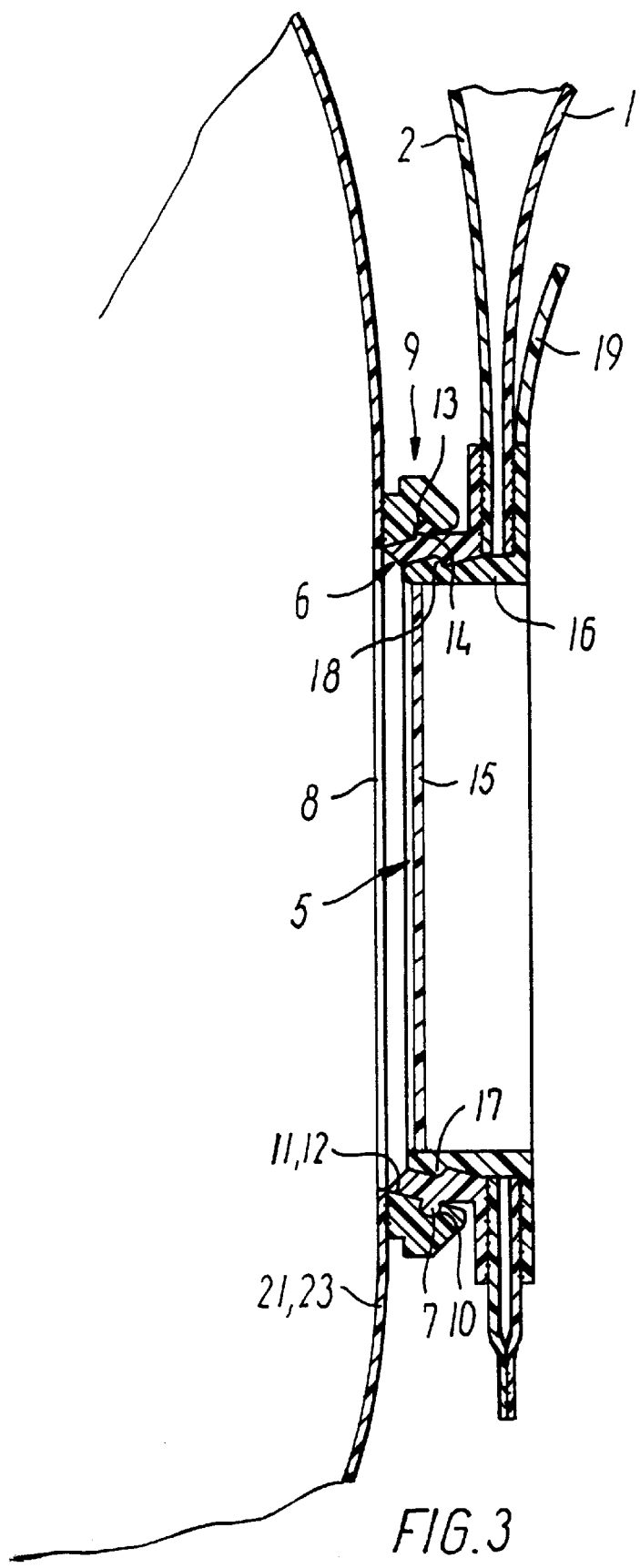
FIG. 3 is an enlarged sectional view of the design of cooperating engagement elements for coupling a coupling ring round the bag outlet opening with another coupling ring on a bag extension.

At the opposite end in relation to the inlet opening 3, the bag is designed with a narrowed end section, where in the second plastic film blank 2 forming the front wall of the bag an outlet opening 5 is formed, which is surrounded by a coupling ring 6 for coupling a bag extension with the bag. For this purpose, as it appears most clearly from FIG. 3, the coupling ring 6 has an outward-facing engagement flange 7 and for coupling with this flange the bag extension of the collecting bag system comprises an inlet opening 8 with a surrounding second coupling ring 9, which for a releasable sealing coupling to the coupling ring 6 of the outlet opening 5 has a corresponding inward-facing engagement part, which in the embodiment shown is designed as an annular track 10 with a cross-sectional profile adapted to the shape of the cross-sectional profile of the outward-facing engagement flange 7 on the coupling ring 6.

As the coupling rings 6 and 9 are designed with some elastic deformation capacity, eg, as injection-moulded rings of polyethylene or similar material, the track 10 for achieving an improved tightness is preferably somewhat undersized in relation to the engagement flange 7 on the coupling ring 6, ie, with its maximum diameter being smaller than that of the engagement flange 7.

The coupling can be further stabilized by designing the track 10 and the engagement flange 7 with sloping contact sides, 11 and 12 respectively, for providing a convergent wedge profile.

To provide a reliable sealing of the two coupling rings 6 and 9, a groove 13 may be provided at the bottom of the track 10 for receiving a tightening bead 14 situated at the outmost periphery of the engagement flange 7. The tightening bead is dimensioned with a slightly larger radius of curvature than the groove 13.

As an important feature of the invention, inside the coupling ring 6 of the bag outlet opening 5 a closing membrane 15 is placed, which is designed with an annular coupling element 16, providing a sealing, but releasable coupling, with an inward-facing engagement element on the coupling ring 6.

In the embodiment shown, the coupling element 16 of the closing membrane 15 is designed with an outward-facing flange 17, and the corresponding engagement element on the coupling ring 6 of the outlet opening 5 is designed as a groove 18 for sealingly receiving the flange 17.

The closing membrane 15 with the coupling element 16 is permanently connected, eg, by adhesion or welding, with the plastic film blank 1 forming the back side of the bag. On the outside of this plastic film blank a catcher flap 19 is mounted for release of the coupling between the coupling element 16 and the groove 18 in the coupling ring 6 of the outlet opening 5.

As described above, the closing membrane 15 means that a bag extension can be coupled to the bag forming a tight connection before passage is provided through the outlet opening 5 to the bag extension.

To enable the use of the collecting bag without a bag extension, an exterior coupling ring 20 can be mounted to the bag front wall 2 above the end section with the outlet opening 5, the coupling ring 20 having a cross-sectional profile largely corresponding to that of the bag extension coupling ring 9, to facilitate coupling of the outlet opening coupling ring 6 when the bag end section is folded up. The collecting bag according to the invention would then not feel larger or more uncomfortable during use than conventional bags.

Figure 4:
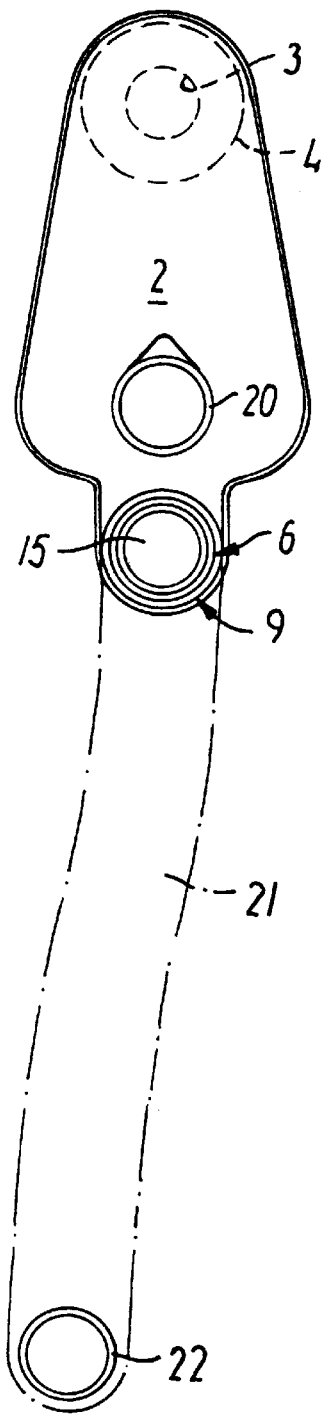
FIG. 4 is a bag extension designed as a coupling tube.

As mentioned, the bag extension of the collecting bag system according to the invention can have different designs. FIG. 4 shows an extension designed as a tubular specimen 21 of plastic film with the coupling ring 9 mounted in one end.

Such an extension can for instance be used as a discharge tube for the bag in order to reduce the risk of contamination and odour nuisances. Such discharge tube may be produced as a disposable product in a water-soluble material with the coupling ring 9 made of a biodegradable material, so that it is possible to flush the discharge tube down the toilet after use.

A tubular specimen as shown in FIG. 4 can also be used for coupling the collecting bag with a collecting bag or tank with larger capacity. For this purpose, the tube 21 may in its opposite end be provided with a coupling ring 22 for coupling with a corresponding coupling ring on the larger collecting bag or tank (not shown).

Figure 5:
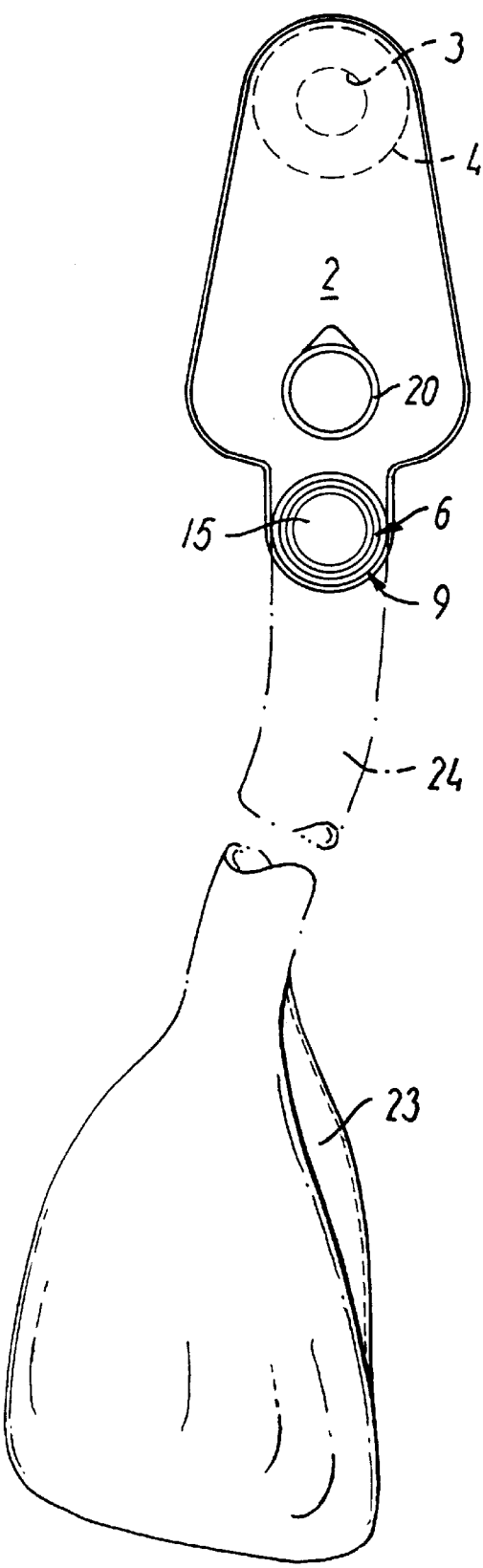
FIG. 5 is an extension device designed as a collecting bag with larger capacity.

As shown in FIG. 5, the bag extension can be designed as a collecting bag 23 with an inlet 24 of varying length to which the coupling ring 9 is attached. Such a bag is well suited as a bedside bag for newly operated patients confined to bed or for patients requiring nursing, but it can also be designed for attachment to the patient's leg to reduce the need for frequent emptying of the bag.

The examples of bag extensions shown and described should not be regarded as delimiting for the invention, as any type of bag extension whatsoever can be used with a coupling ring for coupling with the coupling ring around the bag outlet opening.

Although the invention is shown and described with reference to stoma bags, the collecting bag and the bag system are not limited to this application, but can, subject to a suitable adaption of the coupling ring design, also be used in connection with urine bags and other forms of collecting bags for body wastes.

I claim:

1. A collecting bag for human body wastes comprising a bag member formed by two largely oblong plastic film blanks having joined edges and an inlet opening, connecting elements for connection of the bag to a body orifice, especially a stoma, surrounding said inlet opening, an outlet opening formed in an end section of one of said film blanks separated from said inlet opening, a first coupling ring having an inward-facing engagement element and an outward-facing engagement flange surrounding said outlet opening and providing a releasable, sealing coupling with a second coupling ring having an inward-facing engagement part to engage said engagement flange, means for closing said outlet opening comprising a closing membrane inside said first coupling ring and having an annular coupling element to provide a sealing, but releasable coupling with said inward-facing engagement element, said closing membrane with said annular coupling element being firmly connected with the other of said film blanks, a catcher flap being mounted on the outside of said other film blank opposite said coupling element for releasing the coupling between said annular coupling element and said first coupling ring.

2. A collecting bag as claimed in claim 1, wherein said second coupling ring is mounted on the bag itself on the outside of said one film blank opposite said end section for connection of said first coupling ring with said end section by folding of the latter during use of the collecting bag.

3. A collecting bag as claimed in claim 1, wherein said annular coupling element has an outward-facing flange and said inward-facing engagement element on said first coupling ring comprises a groove for sealingly receiving said flange.

4. A collecting bag as claimed in claim 1, wherein said inward-facing engagement part on the second coupling ring comprises an annular track with a cross-sectional profile the shape of which is adapted to the cross-sectional profile of the outward-facing engagement flange on said first coupling ring.

5. A collecting bag as claimed in claim 4, wherein a maximum diameter of said track is smaller than a maximum diameter of said engagement flange on the first coupling ring.

6. A collecting bag as claimed in claim 4, wherein said track and said engagement flange are formed with sloping contact sides for providing an outwardly convergent wedge profile.

7. A collecting bag as claimed in claim 4, wherein a groove is provided at the bottom of said track for receiving a tightening bead at the outer periphery of the engagement flange.

8. A collecting bag system comprising
a collecting bag for human body wastes comprising a bag member formed by two largely oblong plastic film blanks having joined edges and an inlet opening, connecting elements for connection of the bag to a body orifice, especially a stoma, surrounding said inlet opening, an outlet opening formed in an end section of one of said film blanks separated from said inlet opening, a first coupling ring having an inward-facing engagement element and an outward-facing engagement flange surrounding said outlet opening and providing a releasable, sealing coupling with a second coupling ring having an inward-facing engagement part to engage said engagement flange, means for closing said outlet opening comprising a closing membrane inside said first coupling ring and having an annular coupling element to provide a sealing, but releasable coupling with said inward-facing engagement element, said closing membrane with said annular coupling element being firmly connected with the other of said film blanks, a catcher flap being mounted on the outside of said other film blank opposite said coupling element for releasing the coupling between said annular coupling element and said first coupling ring,
the system further comprising a bag extension member, said second coupling ring being mounted in said extension member.

9. A collecting bag system as claimed in claim 8, wherein an exterior coupling ring is mounted on said one film blank of the collecting bag above said end section, for engagement of said first coupling ring with said end section by folding of the latter during use of the collecting bag without said bag extension member.

10. A bag extension member for a collecting bag system comprising a collecting bag for human body wastes comprising a bag member formed by two largely oblong plastic film blanks having joined edges and an inlet opening, connecting elements for connection of the bag to a body orifice, especially a stoma, surrounding said inlet opening, an outlet opening formed in an end section of one of said film blanks separated from said inlet opening, a first coupling ring having an inward-facing engagement element and an outward-facing engagement flange surrounding said outlet opening and providing a releasable, sealing coupling with a second coupling ring having an inward-facing engagement part to engage said engagement flange, means for closing said outlet opening comprising a closing membrane placed inside said first coupling ring and having an annular coupling element to provide a sealing, but releasable coupling with said inward-facing engagement element, said closing membrane with said annular coupling element being firmly connected with the other of said film blanks, a catcher flap being mounted on the outside of said other film blank opposite said coupling element for releasing the coupling between said annular coupling element and said first coupling ring, said extension member being formed as a tube specimen of plastic film, said second coupling ring being mounted in one end of said extension member.

11. A bag extension member as claimed in claim 10, wherein said tube specimen has in its opposite end a coupling ring for connection to a first coupling ring surrounding said inlet opening for a bag or tank with a larger capacity than the bag connected to the body orifice.

12. A bag extension member as claimed in claim 8, said extension member forming an additional collecting bag with said second coupling ring being directly attachable to said first coupling ring in the collecting bag connected to the body orifice and having a larger capacity than this bag.

13. A bag extension member as claimed in claim 12, wherein said additional collecting bag is provided with means for attachment to the patient's leg.

14. A bag extension member as claimed in claim 12, wherein said additional collecting bag is formed as a disposable discharge bag of a water-soluble film material and said second coupling ring being of a biodegradable material.

15. A collecting bag as claimed in claim 5, wherein said track and said engagement flange are formed with sloping contact sides for providing an outwardly convergent wedge profile.

\* \* \* \* \*